United States Patent [19]

Steppe et al.

[11] Patent Number: 4,713,051
[45] Date of Patent: Dec. 15, 1987

[54] CASSETTE FOR SURGICAL IRRIGATION AND ASPIRATION AND STERILE PACKAGE THEREFOR

[75] Inventors: Dennis L. Steppe, Tustin; Larry L. Hood, Laguna Hills; Gary D. Boggs, Santa Ana, all of Calif.

[73] Assignee: CooperVision, Inc., Palo Alto, Calif.

[21] Appl. No.: 736,335

[22] Filed: May 21, 1985

[51] Int. Cl.$^4$ .............................................. A61M 1/00
[52] U.S. Cl. ...................................... 604/30; 604/34; 604/35
[58] Field of Search ...................... 604/27, 30, 34–35; 128/24 A; 417/360

[56] References Cited

U.S. PATENT DOCUMENTS

| | | | |
|---|---|---|---|
| 3,384,080 | 5/1968 | Muller | 128/214 |
| 3,589,363 | 6/1971 | Banko et al. | 128/24 A |
| 4,142,524 | 6/1977 | Jassawalla et al. | 128/214 |
| 4,178,138 | 12/1979 | Iles | 417/360 |
| 4,187,057 | 2/1980 | Xanthopoulos | 417/63 |
| 4,303,376 | 12/1981 | Siekmann | 417/360 |
| 4,396,385 | 8/1983 | Kelly et al. | 604/152 |
| 4,450,078 | 5/1984 | Farr | 604/152 |
| 4,479,760 | 10/1984 | Bilstad et al. | 417/395 |
| 4,479,761 | 10/1984 | Bilstad et al. | 417/395 |
| 4,493,695 | 1/1985 | Cook | 604/27 |
| 4,493,706 | 1/1985 | Borsanyi et al. | 604/153 |

OTHER PUBLICATIONS

Brochure entitled "The SITE TRX, System 2200 for Anterior Segment Surgery", SITE Microsurgical Systems, Inc.

Advertisement in Ophthalmology Times, Jan., 1982, vol. 7, No. 1.
Brochure entitled "SITE TRX, System Description, Accessories and Price List", Dec., 1981.
Brochure entitled "Start Your Advanced Microsurgical System Now, with an Extraordinary New I/A Unit".
Instruction Manual, for Storz Microvit TM Vitrectomy System, p. 203.
Brochure, "CooperVision System VI" (Showing Disposable Vitrectomy and I/A Cassettes).

*Primary Examiner*—John D. Yasko
*Assistant Examiner*—Gene B. Kartchner
*Attorney, Agent, or Firm*—Vorys, Sater, Seymour & Pease

[57] ABSTRACT

A cassette is structurally adapted to receive at least a portion of an irrigation manifold and an aspiration manifold, so that when the cassette is firmly secured to a cassette mechanism on an emulsifier/aspirator unit: (1) the flow to irrigation solution through the irrigation manifold is regulated; (2) the flow of aspirated fluid and tissue from the surgical site is regulated; (3) the vacuum control system (VCS) within the unit is applied to the aspiration manifold. The cassette defines, at its leading edge, an irrigation opening, an aspiration pump opening, and a vacuum control system opening. The cassette housing defines an irrigation boss having a flat leading edge surface in register with the irrigation opening, while an aspiration boss is located in register with the aspiration pump opening. A cassette mechanism is located on the emulsifier/aspirator unit and is structurally adapted to receive the cassette to complete the fluidic connection upon insertion of the cassette.

16 Claims, 21 Drawing Figures

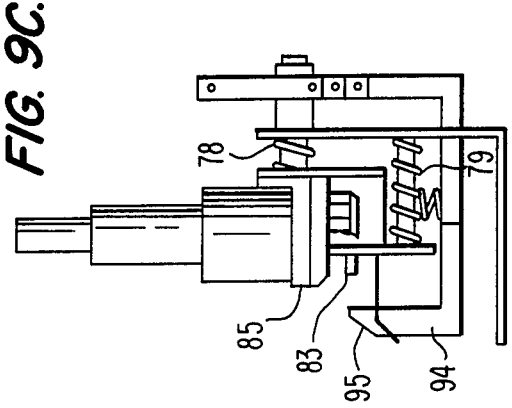
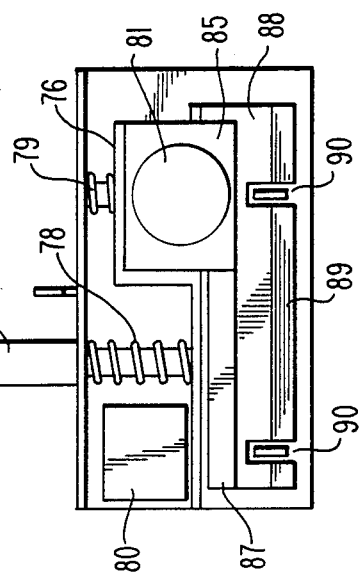
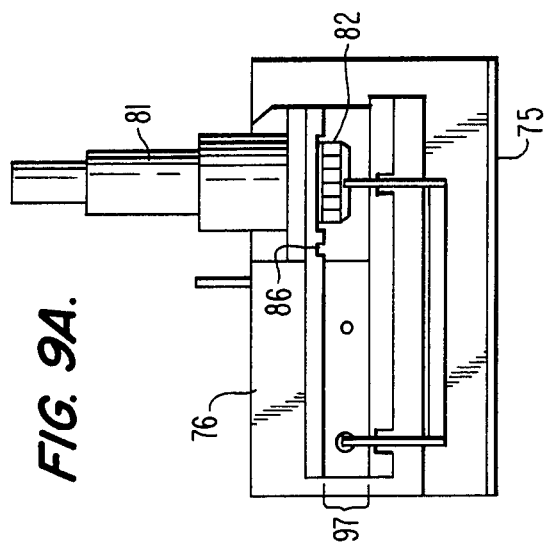
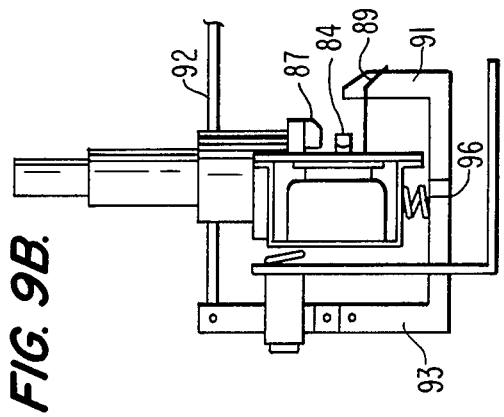

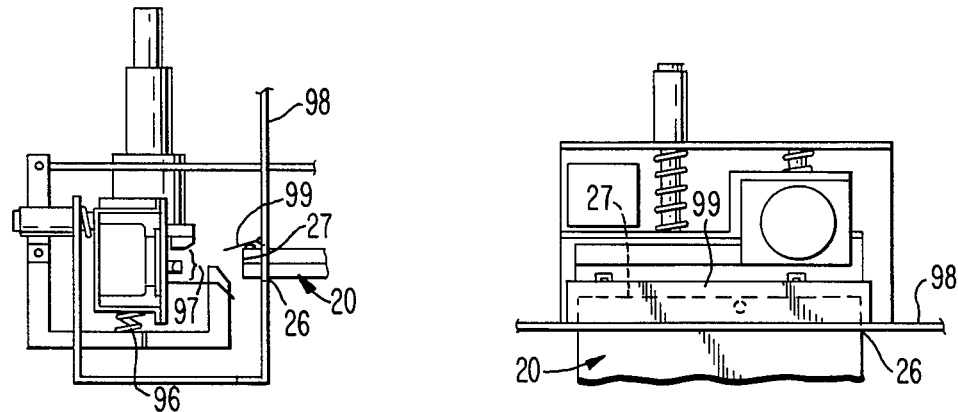
FIG. IIA.
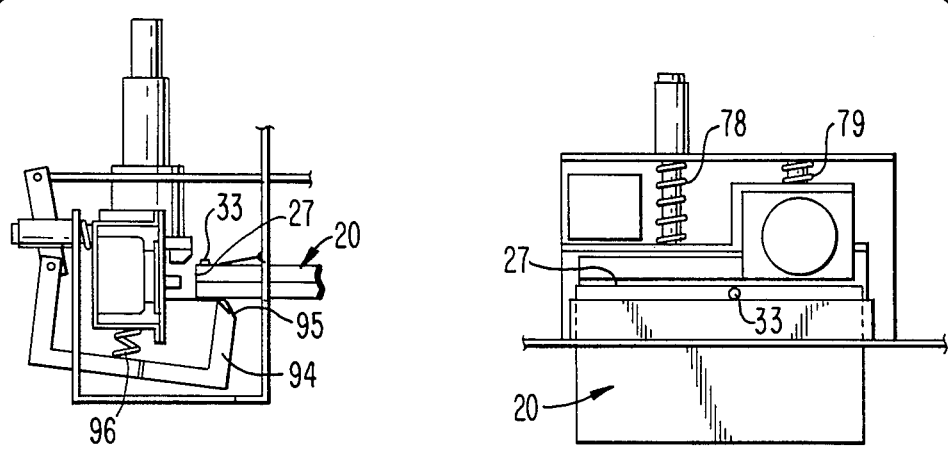
FIG. IIB.
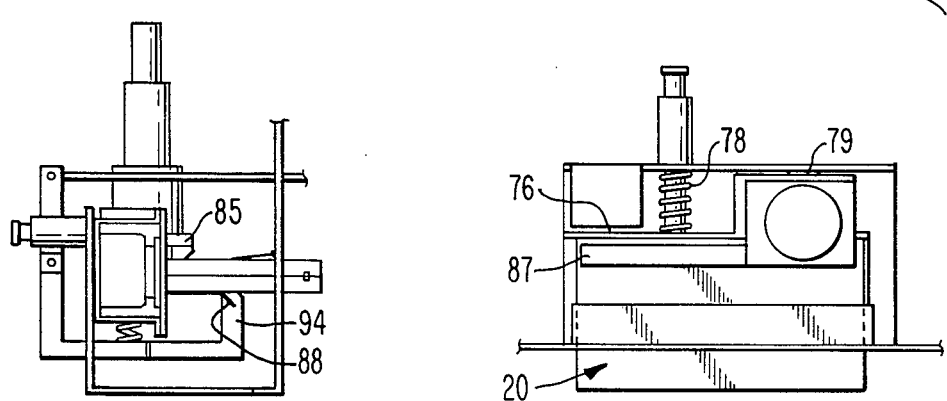
FIG. IIC.

CASSETTE FOR SURGICAL IRRIGATION AND ASPIRATION AND STERILE PACKAGE THEREFOR

BACKGROUND OF THE INVENTION

This invention relates to a cassette for surgical irrigation and aspiration and a sterile package for such cassette. More particularly, this invention relates to a cassette for use with an ocular ultrasonic surgical device. Still more particularly, this invention relates to a cassette for an ultrasonic surgical device wherein the cassette is supplied with both irrigation and aspiration tubes and a waste bag assembled and packaged in a sterile package.

In connection with surgical procedures of various types or, more generally, in connection with medical treatments, a number of various types of apparatuses are known for controlling the flow of fluid from a source to a patient. In such devices, various mechanisms have been developed for controlling the flow of fluid from a source to a patient. In such devices, various mechanisms have been developed for controlling the flow of fluid through a fluid infusion or extraction system at a designated rate. In such systems, it has become desirable, for a number of reasons, to utilize a single use cassette in connection with such devices. In particular, devices are known for use in conjunction with a prepackaged disposable fluid processing module of a type which includes a housing wherein fluid containers, tubing segments, and other components required in the processing of fluid are contained to cooperate with various means for establishing a fluid circuit and controlling the flow of fluid through such a circuit.

On the other hand, an ocular ultrasonic surgical device is known to the art and described generally in U.S. Pat. No. 3,589,363. In that device, a hand-held ultrasonic vibrating tool is used to break apart and remove unwanted material in a surgical procedure especially adapted for surgical operations, such as cataract removal. In such a device, electrical connections are provided for supplying ultrasonic power to the handpiece and fluid connections are provided for controlling the supply of treatment fluid and the aspirative withdrawal of the suspension of tissue particles in the fluid from the operative site. Such devices include regulation techniques to control pressure within limits at the operative site. Thus, emulsifier/aspirator devices have been available to the art for use in connection with cataract surgery.

It is to an improvement in such devices that this invention is primarily directed, by providing a cassette which houses a portion of both the aspiration and irrigation manifolds for a simple yet reliable connection to the emulsifier/aspirator device.

The surgical team that performs a cataract procedure typically consists of a primary surgeon, an optional assistant surgeon, a scrub nurse, an anethesiologist, and a circulator or non-sterile nurse. The primary and assistant surgeons and the scrub nurse directly perform the cataract procedure and are in the sterile field. Since a cataract procedure requires transfers between the sterile and non-sterile fields, the circulator acts as the liaison for the surgical team between the sterile and the non-sterile fields. A responsibility of the circulator is to deliver sterile items, such as disposables or emergency surgical devices, to the sterile field and accept transfer of components necessary to set up the equipment being used.

In connection with prior art ophthalmic procedures, the circulator generally opened a package or packages sometimes in the form of pouches or trays, that contained the irrigation and aspiration manifolds for use in the ophthalmic procedure, and aseptically transferred them to the sterile field. The scrub nurse then located those ends of each manifold that required connection to the instrument and, while holding each manifold at a different time, transferred each manifold back to the circulator who respectively connected the irrigation manifold to an irrigation solenoid located on the equipment. A vent chamber on the irrigation manifold was then inserted into an appropriate irrigation source and the manifold was suspended on an IV pole. Thereafter, the circulator connected the aspiration manifold to the vacuum control system and to a rotary peristaltic pump located on the equipment. The circulator then took the manifold exiting the peristaltic pump and placed its end into a drainage bag which the circulator had previously attached to the equipment. At this point, the manifolds were ready for priming and system checkout.

Thus, in connection with the apparatus of the prior art, the set up procedure prior to this invention consisted of five connections made by the circulator to the equipment. Two of the connections were for the irrigation manifold and three were for the aspiration manifold. The attachment of the irrigation manifold to the irrigation solenoid consisted of inserting the irrigation tubing in the irrigation solenoid. In addition, attachment of the silicone pump tubing on the aspiration manifold to the aspiration pump roller assembly on the equipment also required dexterity and knowledge of equipment functions. If either the vacuum control connection or the pump connection were improperly made, the aspiration manifold might be unable to achieve a proper vacuum during the surgical procedures.

The number of transfers required prior to this invention were variable, requiring three or four transfers, and depended upon the exact method of packaging. If the manifolds were packaged in separate single pouches, then the circulator opened each outer pouch and transferred each inner pouch into the sterile field. Either of these two methods required two separate transfers into the sterile field. If the manifolds were packaged so that they were doubly-wrapped in trays, only one transfer was required into the sterile field. However, in any case, once the manifolds are in the sterile field, the scrub nurse must locate those ends of each manifold that must be transferred one at a time back to the circulator for equipment setup. In addition, extreme care must be taken when individually transferring the manifolds to avoid a risk of contamination of the scrub nurse or sterile field.

Thus, it is an overall object of this invention to provide a cassette for use in connection with a surgical procedure which makes convenient an interchange between the sterile and non-sterile fields in an ophthalmic procedure.

It is another object of this invention to provide a cassette which minimizes the steps between the sterile and non-sterile fields to prepare the aspiration and irrigation manifolds ready for priming and system checkout.

It is another object of this invention to provide a cassette for use with an ophthalmic device to minimize the connections made to the equipment.

It is still another object of this invention to provide a cassette which houses a portion of each of the irrigation and aspiration tubing together with a drain bag structured so that all fluidic connections are precisely made to the equipment by insertion of the cassette into the equipment, so that the reliability of the fluidic connections is transferred from a person to the construction and geometry of the cassette and mating cassette mechanism.

It is still another object of this invention to provide packaging for the cassette which limits the minimum number of transfers to two, i.e. a transfer of a transfer tray into the sterile field and a transfer of a transfer tray and the remaining portion of the cassette back to the non-sterile field so that the remaining portion of the cassette stays in the transfer tray during this transfer, thus reducing the risk of contamination.

These and other objects of the invention will become apparent from the following written description of the invention taken together with the accompanying drawings.

BRIEF SUMMARY OF THE INVENTION

Directed to achieving the aforementioned objects and improving an emulsifier/aspirator known to the art, a cassette according to this invention is structurally adapted to receive at least a portion of an irrigation manifold and an aspiration manifold, so that when the cassette is firmly secured to a cassette mechanism on an emulsifier/aspirator unit: (1) the flow of irrigation solution through the irrigation manifold is regulated; (2) the flow of aspirated fluid and tissue from the surgical site is regulated; and (3) the vacuum control system (VCS) within the unit is applied to the aspiration manifold to limit vacuum levels attainable in the aspiration manifold. The cassette is preferably injection molded to form a top cassette housing and a bottom cassette housing together defining, at its leading edge, an irrigation opening, an aspiration pump opening, and a vacuum control system opening. The bottom cassette housing defines an irrigation boss having a flat leading edge surface in register with the irrigation opening, while an aspiration boss is located in register with the aspiration pump opening. Means are provided for securing the top cassette housing to the bottom cassette housing. The cassette further defines a drainage bag opening on the trailing edge of the cassette so that the cassette when ready for use houses portions of the irrigation and aspiration manifolds, as well as the drain bag.

A cassette mechanism, located on the emulsifier/aspirator unit, is structurally adapted to receive the cassette and comprises a cassette latch bracket and a solenoid/pump mounting plate for mounting an irrigation solenoid, an aspiration pump and roller assembly, and VCS fitting. Means for latching the cassette in the cassette mechanism are also provided so that the cassette mechanism provides an opening which accepts the leading edge of the cassette. When the cassette is firmly secured to the cassette mechanism, an occluder shaft of the irrigation solenoid passes through the irrigation opening of the cassette to occlude the irrigation tubing against the flat leading surface of the irrigation boss in the cassette, thus to control the flow of irrigation solution through the irrigation manifold by compressing the irrigation tubing between the occluder shaft and the irrigation boss. When the irrigation solenoid is energized, the occluder shaft is withdrawn, allowing the irrigation tubing to open and irrigation flow to occur.

When the cassette is firmly attached to the cassette mechanism, a roller assembly of the aspiration pump cooperates with the aspiration pump opening of the cassette to occlude the aspiration pump tubing against the aspiration boss, thus to effect flow of aspirated tissue and fluid through the aspiration manifold by the roller assembly of the aspiration pump. Since the aspiration pump tubing is compressed between the rollers of the roller assembly of the aspiration pump, when the aspiration pump is energized, rotation of the roller assembly forces fluid and tissue to flow from the surgical site.

Insertion of the cassette into the emulsifier/aspirator unit also allows a vacuum control system within the unit to limit vacuum levels attainable in the aspiration manifold by effecting a sealed connection between a VCS fitting mounted on the cassette mechanism which cooperates with a VCS connection on the cassette. Thus, insertion of the cassette into the cassette mechanism causes irrigation, aspiration, and vacuum fluidic connections to be readily made.

A sterile package in the form of a transfer tray receives the prepared cassette, drain bag, irrigation tubing and aspiration tubing and is sealed so that removal of the outer tray lid permits the aseptic transfer of the transfer tray to the sterile field. Retention of portions of the irrigation tubing and aspiration tubing inside the cassette housing permits the retransfer of the transfer tray and remaining portion of the cassette to the non-sterile field for insertion into the equipment for connections by insertion of the cassette as described.

The method of making and using such a cassette and the operative procedures for establishing connections are also described.

BRIEF DESCRIPTION OF THE DRAWINGS

In the drawings:

FIG. 9 is a diagrammatic view of the structural features of the cassette mechanism on the emulsifier/aspirator unit shown in FIG. 1, wherein FIG. 9A is a front pictorial view; FIG. 9B is a left side pictorial view; FIG. 9C is a right side pictorial view; and FIG. 9D is a top pictorial view, together showing the components of the cassette mechanism for receiving the cassette according to the invention;

FIG. 11 is a view of the interfacing between the cassette mechanism of FIGS. 9 and 10 and the cassette of FIGS. 2–7 wherein FIGS. 11A, 11B, and 11C illustrate various stages of the insertion of the cassette into the cassette mechanism;

DETAILED DESCRIPTION OF THE PREFERRED EMBODIMENTS

Figure 1:
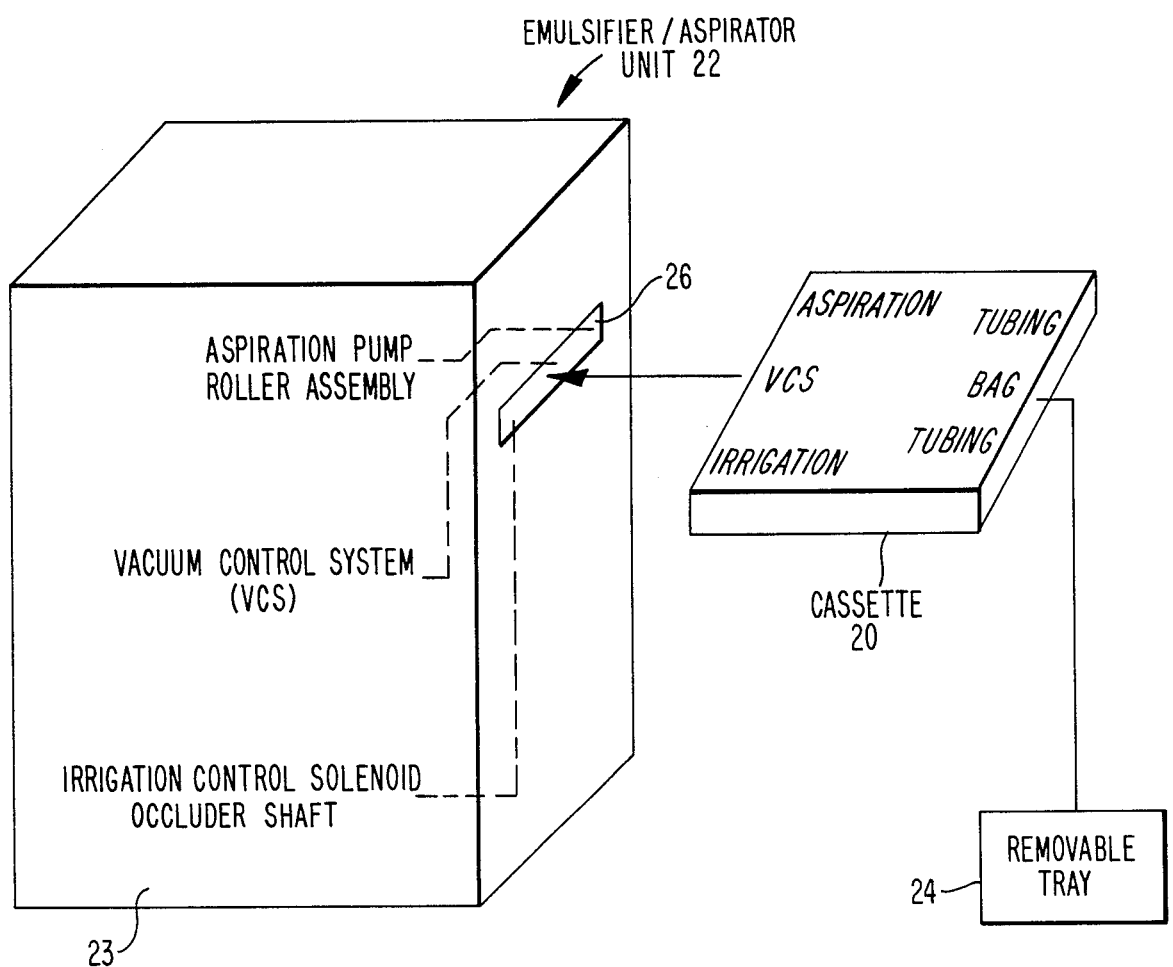
FIG. 1 is a stylized schematic of an emulsifier/aspirator unit incorporating a cassette receiving section for receiving a cassette according to the invention and showing the fluidic connections achieved by insertion of the cassette into the unit.

A cassette for surgical irrigation and aspiration is shown generally in FIG. 1 by the reference numeral 20. The cassette is used with an occular ultrasonic surgical device, designated generally by the reference numeral 22, generally referred to in the art as an emulsifier/aspirator. The device uses a hand held ultrasonic vibrating tool of the type shown in U.S. Pat. No. 3,589,363, the disclosure of which is incorporated by reference, to breakup a cataractous crystalline lens in the eye and aspirate the fragments. The unit 22 includes a cabinet 23 which houses suitable electronic circuitry for supplying ultrasonic power to a handpiece, and controls for the irrigation fluid, and for the aspiration suction, as will be discussed in greater detail. The cassette 20 is supplied equipped with the irrigation and aspiration tubes and a waste bag all assembled and packaged in a removable sterile package 24. The cassette 20 is removed from the sterile package 24 in the operating room, the appropriate ends of the tubes on the cassette are connected with a minimum number of transfers and connections, and the cassette is inserted into a slot 26 in the side of the control cabinet 23 of the emulsifier/aspirator unit 22. The remaining tube connection is made to a source of fluid.

As depicted generally in FIG. 1, the cassette carries a portion of both of the irrigation manifold and the aspiration manifold, in a structural cooperation with an irrigation opening, an aspiration opening, and a VCS opening defined on the leading edge of the cassette 20. The emulsifier/aspirator unit 22 includes an irrigation solenoid having an occluder shaft, an aspiration pump, and a vacuum control system. Insertion of the cassette 20 (after removal from the tray 24) into the slot 26 causes a cooperation between the cassette 20 and the cassette mechanism to: (1) achieve a control of the flow through the irrigation manifold by the coaction of an occluder shaft on an irrigation solenoid cooperating with the tubing through an irrigation opening in the cassette; (2) to effect a flow through the aspiration manifold by the coaction with an aspiration pump cooperating with an aspiration opening on the cassette; and (3) to apply VCS control for the unit 22 to the aspiration tubing through a VCS opening on the cassette. Thus, insertion of the cassette into the cassette mechanism establishes and controls the fluidics of the system.

Figure 2:
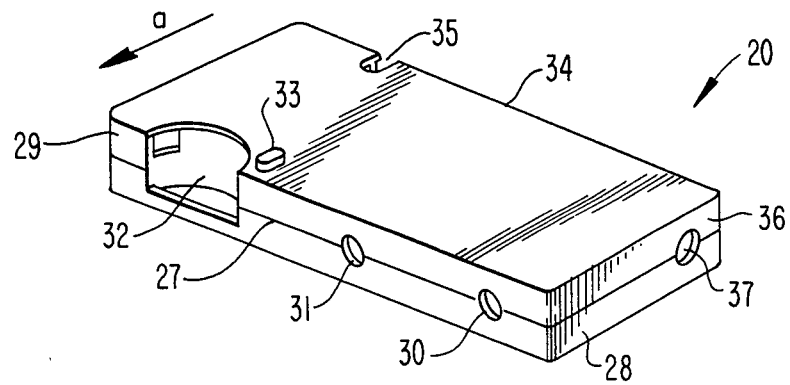
FIG. 2 is a perspective view of a cassette according to the invention.
Figure 3:
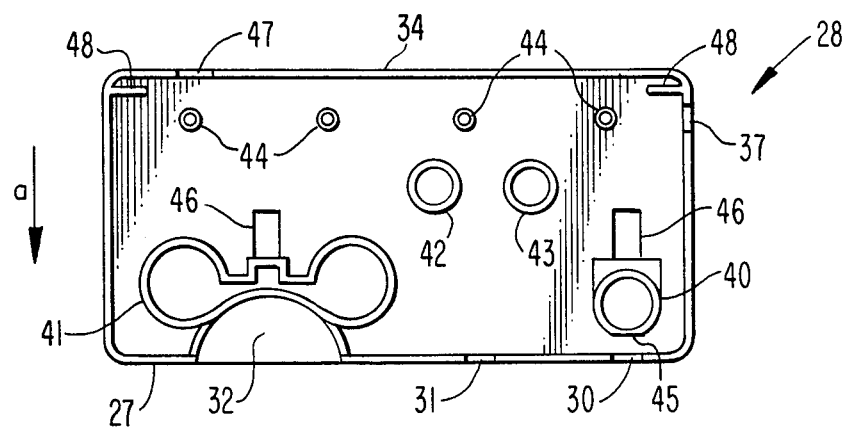
FIG. 3 is a view of the inside of the bottom cassette housing.
Figure 4:
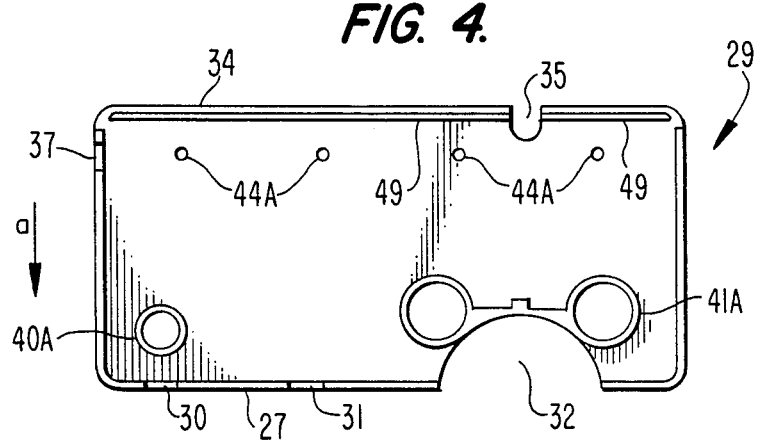
FIG. 4 is a view of the inside of the top cassette housing.

FIGS. 2–4 collectively show the structure of the cassette 20. The cassette 20 is preferably an injected molded housing made from a suitable plastic material and comprises a bottom cassette housing 28 and a top cassette housing 29 which are structurally compatible to define at the leading edge 27 thereof an irrigation opening 30, a vacuum control system opening 31, and an aspiration pump opening 32. The term "leading edge" refers to the forwardmost edge of the cassette in the direction of insertion into the unit 22 as shown by the arrow labeled with the reference character a. The upper surface of the cassette 20 defines a boss 33, and the trailing edge 34 of the unit defines an irrigation manifold opening 35.

A lateral edge 36 of the cassette 20 defines an irrigation and aspiration manifold opening 37. The respective openings 32, 31, 30, 35, and 37 are preferably formed by positioning complementary openings located in the respective and mating edges of the top and bottom cassette housings 29 and 28.

As shown in FIG. 3, the bottom cassette housing 28 defines on the bottom surface thereof a female irrigation boss 40, a female aspiration boss 41, a pair of strain relief bosses 42, 43, and a plurality of female drain bag bosses 44. The irrigation boss 40 has a flat leading edge surface 45 located near the leading edge of the cassette. The irrigation opening 30 is located directly forward of and in register with the surface 45 to define one half of the irrigation opening 30, the other half of which is defined by the top cassette housing 29. As will be seen, the surface 45 cooperates with an occluder shaft on an irrigation solenoid to control flow through an irrigation manifold positioned adjacent to the surface 45, when the cassette 20 is inserted into the unit 22.

A semi-circular aspiration pump opening 32 is located directly in front of the female aspiration boss 41. The pump opening 32 cooperates, when the cassette 20 is inserted into the unit 22, with an aspiration pump to effect flow through the aspiration tubing.

The vacuum control system (VCS) opening 31 is located between the aspiration pump opening 32 and the irrigation opening 30 along the leading edge of the cassette 20. The opening 31 allows the VCS system on the unit 22 to control the suction vacuum of the aspiration of tissue caused when the cassette 20 is inserted into the unit 22.

The irrigation and aspiration manifold opening 37 is defined in the lateral edge 36 of the cassette 20. A pair of rectangular latch openings 46 are also located on the bottom cassette housing 28. One latch opening 46 is located behind the female irrigation boss 40, while the other latch opening 46 is located behind the female aspiration boss 41. The trailing edge 34 also defines in the bottom cassette housing 28 a drainage bag opening 47. A pair of female slots 48 are also located on opposite sides of the trailing edge 34 of the bottom cassette housing 28.

The top cassette housing 29 as shown in FIG. 4 defines a male irrigation boss 40A, a male aspiration boss 41A, a plurality of male drainage bag bosses 44A, and an elongated drainage bag hold down member 49. The leading edge 27 of the top cassette housing 29 respectively defines the complementary portions of the irrigation opening 30, the VCS opening 31, and the aspiration pump opening 32. The respective housings shown in FIGS. 3 and 4 are secured to define the cassette 20 shown in FIG. 1. Thus, the structural portions of the cassette have been described.

Figure 5:
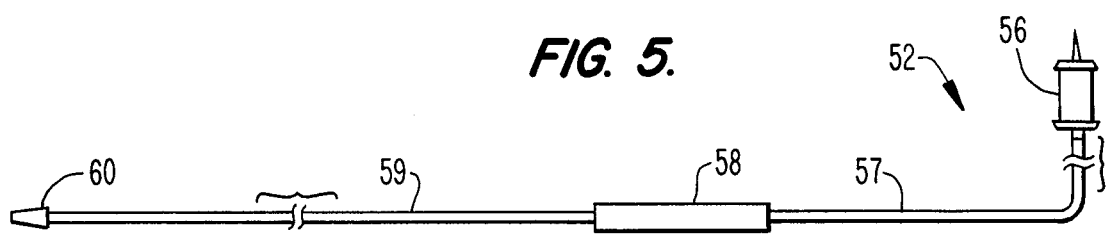
FIG. 5 is a diagrammatic view of an irrigation manifold used in connection with the invention.
Figure 6:
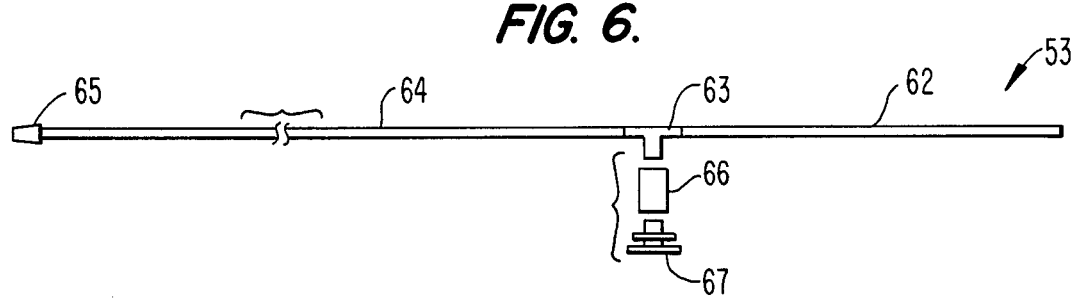
FIG. 6 is a diagrammatic view of an aspiration manifold used in connection with the invention.
Figure 7:
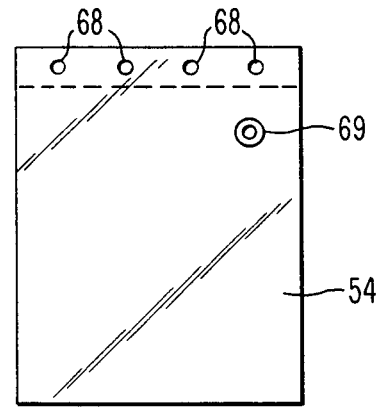
FIG. 7 is a diagrammatic view of a drain bag used in connection with the invention.
Figure 10:
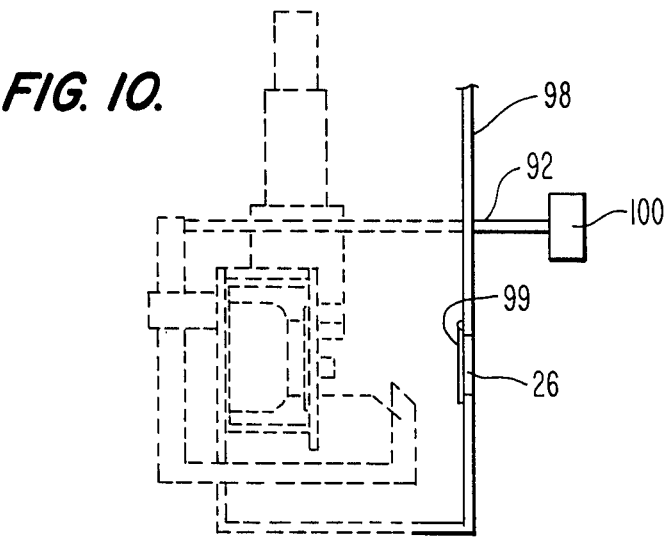
FIG. 10 is side view, diagrammatically illustrated, showing the cassette mechanism of FIG. 9 mounted on the emulsifier/aspirator unit of FIG. 1.

FIGS. 5, 6, and 7 respectively show diagrammatic views of an irrigation manifold 52, an aspiration manifold 53, and a drain bag 54. As will be seen, the cassette 20 shown in FIGS. 1–3 houses a portion of the irrigation manifold 52 and a portion of the aspiration manifold 53, as well as portions of the drain bag 54. As shown in FIG. 5, the irrigation manifold 52 includes a drip chamber 56 connected to an irrigation tube 57, an irrigation silicone tubing 58, and a second segment of irrigation tubing 59, terminating in a male luer fitting 60. Preferably, the tubing sections 57 and 59 are made from polyvinyl chloride (PVC).

As shown in FIG. 6, the aspiration manifold 53 is similarly constructed. The aspiration manifold 53 consists of a length of aspiration pump silicone tubing 62, connected to a plastic tee 63, aspiration PVC tubing 64, and a male luer fitting 65. A check valve 66 and a VCS grommet 67 are also connected to the tee section of the plastic tee 63.

Figure 8:
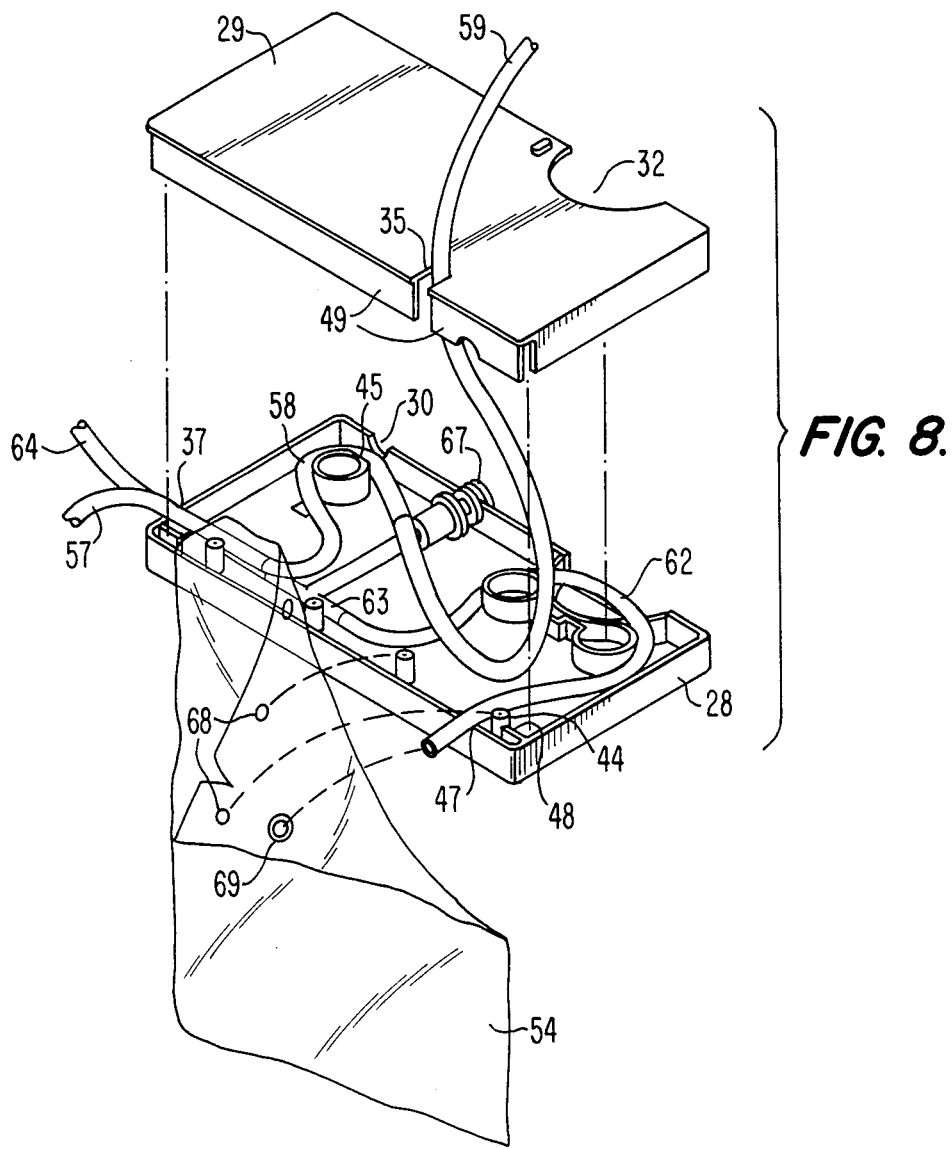
FIG. 8 is an exploded perspective view of the bottom and top cassette housings of FIGS. 3 and 4 when combined with the irrigation manifold, aspiration manifold, and drain bag of FIGS. 5-7 to form a cassette/manifold assembly.

FIG. 7 is a diagrammatical illustration of the drain bag for receiving aspiration products when the system is in use. The drain bag 54 is a polyethylene plastic bag which has a plurality of openings 68 located along the top and which are preferably of a like number to the members 44 and 44A shown in FIGS. 3 and 4 in the cassette housings 28 and 29. The drain bag 54 also includes a drain plug 69 heat sealed to one leaf of the bag. The assembly of the cassette shown in FIGS. 2-4 and the manifolds and drain bag shown in FIGS. 5-7 is thus shown in FIG. 8.

The irrigation PVC tubing 59 enters the cassette 20 through the irrigation manifold opening 35 in the top cassette housing 29. The irrigation silicone tubing 58 is routed around the female irrigation boss 40 between the irrigation opening 30 and the irrigation boss flat leading edge surface 45. From that location, the irrigation silicone tubing 58 is routed around one strain relief boss 42 where it joins the irrigation PVC tubing 57 and exits the cassette through the irrigation and aspiration manifold opening 37.

The aspiration PVC tubing 64 also enters the cassette through the irrigation and aspiration manifold opening 37. The plastic tee 63 is placed between the two strain relief bosses 42, 43. The VCS grommet 67 fits within the VCS opening 31 in the leading edge of the cassette 20. The aspiration manifold silicone tubing 62 (from the tee 63) is routed around the female aspiration boss 41 through the semicircular aspiration pump opening 32. From that location, the aspiration pump tubing 62 joins the drain plug 69 located on the drain bag 54.

The drain bag 54 itself is attached to the bottom cassette housing 28 by placing the four female drain bag bosses 44 (FIG. 3) through the corresponding openings 68 on the drain bag 54. The drain bag and the attached aspiration pump tubing 62 fit through the drainage bag opening 47 on the trailing edge of the cassette 20.

With the tubing thus positioned, the top cassette housing 29 is press fitted into the bottom cassette housing 28 to secure by friction fit the female aspiration boss 41 and the male aspiration boss 41A; the female irrigation boss 40 and male irrigation boss 40A; the two opposed female slots 48; and the drainage bag hold-down 49. The four male drainage bag bosses 44A fit inside the corresponding four female drainage bag bosses 44, thus entrapping the drain bag 54 to the assembled cassette 20.

As shown diagrammatically in FIG. 9 (i.e. in FIGS. 9A-9D), the cassette mechanism consists of two major components: a cassette latch bracket 75 and a solenoid/pump mounting plate 76. The cassette latch bracket 75 is stationary whereas the solenoid/pump mounting plate 76 is movable and is attached to the cassette latch bracket 75 by a bearing 77 and springs 78, 79.

The solenoid/pump mounting plate 76 provides for mounting of an irrigation solenoid 80, an aspiration pump 81 and its associated roller assembly 82, and a VCS fitting 83. An occluder shaft 84 of the irrigation solenoid 80 passes through an opening of the solenoid/pump mounting plate 76. The aspiration pump 81 and roller assembly 82 are mounted to the solenoid/pump mounting plate 76 by a bearing mounting plate 85. The bearing mounting plate 85 defines a slot 86 and beveled edge 87. A cassette guide 88 is also mounted to the solenoid/pump mounting plate 76. The cassette guide 88 defines a beveled facing edge 89 and includes two slots 90.

The cassette latch bracket 75 provides for mounting of the solenoid/pump mounting plate 76 and a cassette latching mechanism 91. The cassette latching mechanism 91 includes a release arm 92, associated linkage 93, and two latch arms 94. The trailing edges 95 of each latch arm 94 are beveled. Both latch arms 94 protrude above the level of the cassette guide 88. A spring 96 connects the latching mechanism 91 to the solenoid pump mounting plate 76.

The entire assembled cassette mechanism provides an opening 97 which accepts the leading edge 27 of the cassette 20. The beveled edge 87 of the bearing mounting plate 85 provides the upper surface of the opening 97 and the cassette guide 88 provides the lower surface of the opening 97. Located between these upper and lower surfaces are the occluder shaft 84 of the irrigation solenoid 80, the VCS fitting 83, and the roller assembly 82 of the aspiration pump 81. Thus, the structure of the cassette mechanism located on the emulsifier/aspirator unit 22 for receiving the cassette 20 to provide the described fluidic connection has been described.

The cassette mechanism of FIG. 9 is mounted to the unit 22 behind a protective panel 98 attached to the unit 22. The protective panel 98 has an opening 26 through which the leading edge 27 of the cassette 20 is inserted. Located behind this opening 26 is a spring-biased door 99 which swings upward and out of the way when the cassette 20 is inserted and automatically closes the opening 26 when the cassette 20 is removed.

An opening in the protective panel 98 located at a position through which passes the release arm 92 of the cassette latching mechanism 91. A release knob 100 is attached to the end of the release arm 92.

Figure 12:
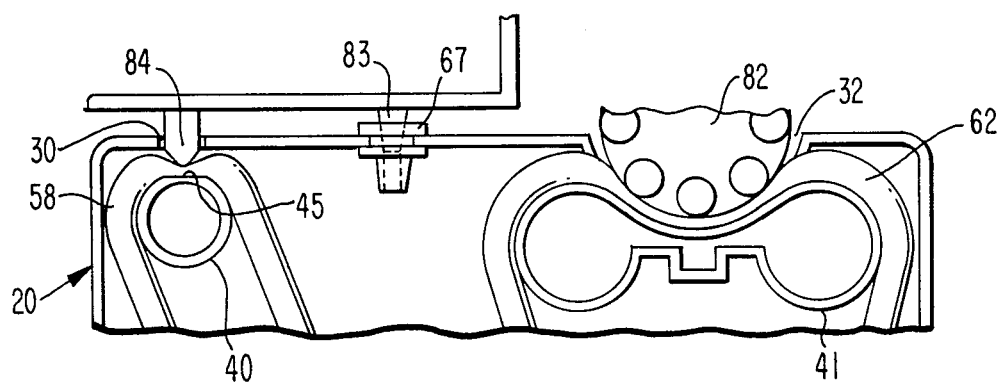
FIG. 12 is a partial view of the fluidic connections between the cassette and the cassette mechanism when the cassette is completely inserted into the cassette mechanism on the emulsifier/aspirator unit.

The interfacing between the cassette 20 and the cassette mechanism is shown in FIGS. 11 and 12.

As shown in FIG. 11A, the leading edge 27 of the cassette 20 is inserted through the opening 26 of the protective panel 98 attached to the unit 22. As the cassette 20 is pushed forward, the spring-biased door 99 is pushed upward and out of the way.

As shown in FIGS. 11 and 12, as the leading edge 27 of the cassette 20 advances, it pushes the beveled trailing edges 95 of the latch arms 94 downward to a position beneath the cassette 20 and the spring 96 is stretched. As the cassette 20 is continued to be pushed forward as shown in FIG. 11C, the leading edge 27 enters the opening 97 delineated by the beveled edge of the bearing mounting plate 85 and the cassette guide 88. The boss 33 on the leading edge 27 of the cassette 20 (FIGS. 2-4) enters the slot 86 located on the bearing mounting plate 85.

Continued forward motion of the cassette causes the leading edge 27 of the cassette 20 to come into contact with the solenoid/pump mounting plate 76. As the springs 78 and 79 are compressed, the entire solenoid/pump mounting plate 76 moves rearwardly, allowing the latch arms 94 to enter the rectangular latch openings 46 (FIG. 3) located on the bottom housing 28 of the cassette 20.

At this point, as best seen in FIG. 12, the cassette 20 is firmly attached to the cassette mechanism. The occluder shaft 84 of the irrigation solenoid 80 passes through the irrigation opening 30 of the cassette 20 and occludes the irrigation silicone tubing 58 against the flat leading edge surface 45 of the irrigation boss 40. The roller assembly 82 of the aspiration pump 81 occupies the semi-circular aspiration pump opening 32 of the cassette 20 and occludes the aspiration pump silicone tubing 62 against the aspiration boss 41 (FIG. 3). The compression force arises from compression of the springs 78 and 79. The VCS fitting 83 passes through the lumen of the VCS grommet 67 (FIG. 6) and is self-sealing. At this point, all fluidic connections are made upon complete insertion of the cassette into the cassette mechanism of the emulsifier/aspirator.

The system fluidics can now be discussed, based on FIGS. 5I∝8 and 12. The irrigation manifold 52 provides for the flow of irrigation fluid to the surgical site. The irrigation manifold 52 connects to an irrigation source (not shown) via the drip chamber 56. The irrigation fluid is delivered to the surgical site via a connection to the male luer fitting 60.

The flow of irrigation solution through the irrigation manifold 52 is thus regulated by the occluder shaft 84 of the irrigation solenoid 80. When the cassette 20 is attached to the cassette mechanism (FIGS. 11A; 11B; 11C), the irrigation silicone tubing 58 is compressed between the occluder shaft 84 and the irrigation boss 40, thus preventing flow of irrigation fluid. When the irrigation solenoid 80 is energized, the occluder shaft 84 moves to a withdrawn position, allowing the lumen of the irrigation silicone tubing 58 to open and irrigation flow to occur within the tubing. Thus, flow of irrigation fluid is controlled.

The aspiration manifold 53 provides for the regulated flow of aspirated fluid and tissue from the surgical site. The aspirated fluid and tissue is removed from the surgical site via a connection to the female luer fitting 65.

The flow of aspirated tissue and fluid through the aspiration manifold 53 is effected by the roller assembly 82 of the aspiration pump 81. When the cassette 20 is attached to the cassette mechanism (FIGS. 11A; 11B; 11C), the aspiration pump silicone tubing 62 is compressed between the rollers of the roller assembly 82 and the aspiration boss 41. When the aspiration pump 81 is energized, the roller assembly 82 rotates in a counter-clockwise direction (as viewed in FIG. 12) forcing fluid and tissue to flow from the surgical site.

Figure 13:
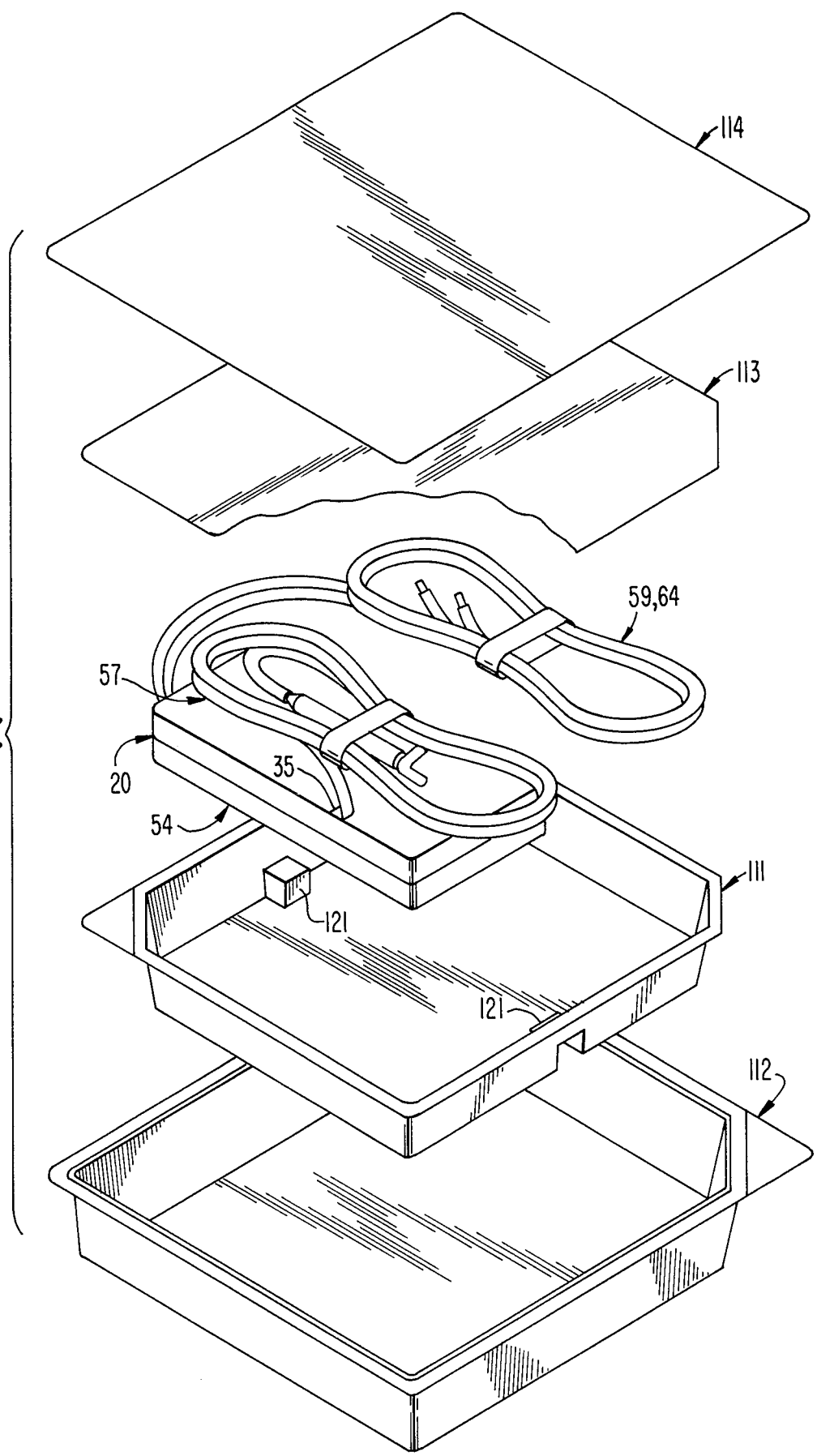
FIG. 13 is an exploded view of the packaging for the cassette according to the invention.

The vacuum control system (VCS) located inside the unit limits vacuum levels attainable in the aspiration manifold 53. The VCS fitting 83 mounted on the cassette mechanism is connected to the VCS of the unit. A sealed connection is effected between the VCS fitting 83 on the cassette mechanism and the VCS grommet 67 on the cassette 20 when the cassette is attached to the cassette mechanism as described. In turn, the VCS grommet 67 is attached to the aspiration manifold 53 via the plastic tee 63 (FIG. 6). A check valve 66 inserted between the VCS grommet 67 and the plastic tee 63 (FIG. 6) prevents backflow of aspirated fluid and tissue from the aspiration manifold 53 to the VCS and completes the fluidic circuit. Thus the fluidic connections for the system are readily made upon insertion of the cassette 20 into the cassette mechanism. Reference may now be made to FIG. 13 for a discussion of the packaging for the cassette.

Packaging of the cassette 20 consists of a transfer tray 111, an outer tray 112, a transfer tray lid 113, and an outer tray lid 114, as shown in perspective in FIG. 3.

The cassette 20 is prepared for placement in the transfer tray 111 by coiling and banding the irrigation PVC tubing 57, which exits the cassette 20 from the irrigation manifold opening 35, and by coiling and banding the irrigation PVC tubing 59 and aspiration PVC tubing 64 which exits the cassette 20 from the irrigation and aspiration manifold opening 37. The drain bag 54 is wrapped around the cassette 20.

The prepared cassette 20 is then placed into the transfer tray 111 placing the cassette 20, the drain bag 54, and the banded irrigation PVC tubing on one side of the transfer tray 111, and the banded irrigation PVC tubing 59 and aspiration tubing 64 on the other. The transfer tray 111 has formed protuberances 121 on its sides which immobilize the cassette 20. The filled transfer tray 111 is then sealed with a transfer tray lid 113 along its perimeter. The filled and sealed transfer tray 113 is then placed into an outer tray 112 which in turn is sealed with an outer tray lid 114.

This entire assembly is then sterilized by a suitable process, preferably with ethylene oxide (ETO) gas. After sterilization, the transfer tray 111 and its contents are sterile.

Use of the sterilized transfer tray 111 during a surgical procedure can now be described.

A typical transfer between the circulator and scrub nurse and equipment set up by the circulator with the invention is as follows. The circulator removes the outer tray lid 114 from the outer tray 112 and aseptically transfers the sterile transfer tray 111 to the sterile field. The scrub nurse removes the transfer tray lid 113 from the transfer tray 111 and removes the banded irrigation PVC tubing 59 and aspiration PVC tubing 64. The scrub nurse then transfers the transfer tray 111 and remaining portion of the cassette 20 back to the circulator.

The circulator removes the cassette 20 from the transfer tray 111 and inserts the cassette 20 into the opening 26 of the protective panel 98 as previously described until a distinct snap is felt. The circulator then removes the banding from the PVC irrigation tubing, inserts the drip chamber 56 into an appropriate irrigation source and suspends it on a pole. At this point, the manifolds are ready for priming and system checkout.

In contrast to the prior art setup, the setup procedure using the invention consists of only two connections that the circulator must make to the equipment; i.e. insertion of the drip chamber 56 to an appropriate irrigation source and the insertion of the cassette 20 into the equipment. At this point, all fluidic connections are precisely made to the equipment, as described. The responsibility of the reliability of the fluidic connections is thus removed from the circulator and is transferred to the specific construction and geometry of the cassette 20 and cassette mechanism previously described.

In contrast to the number of transfers between the sterile and non-sterile field, the packaging of the invention limits the minimum number of transfers to two; i.e. the transfer of the tray 111 into the sterile field and the transfer of the transfer tray 111 and remaining portion of the cassette 20 back to the non-sterile field. Since the remaining portion of the cassette 20 remains in the transfer tray 111 during this transfer, this reduces the risk of contamination to the scrub nurse or sterile field since the transfer tray presents a large surface area to hold and grab on to.

The invention may be embodied in other specific forms without departing from its spirit or essential characteristics. The present embodiments are, therefore, to be considered in all respects as illustrative and not restrictive, the scope of the invention being indicated by the claims rather than by the foregoing description and all changes which come within the meaning and range of the equivalents of the claims are therefore intended to be embraced therein.

What is claimed is:

1. In combination:
    a cassette having a housing defining an irrigation opening, an aspiration pump opening, and a VCS opening, the housing of said cassette defining an irrigation boss in register with said irrigation opening and having a leading edge surface;
    a portion of an irrigation manifold located intermediate said leading edge surface of said irrigation boss and said irrigation opening;
    an aspiration boss located in register with said aspiration pump opening;
    a portion of an aspiration manifold connected intermediate said aspiration pump opening and said aspiration boss;
    a cassette receiving mechanism which includes an irrigation solenoid having an occluder shaft, an aspiration pump and roller assembly, and a vacuum control system which includes a vacuum control system fitting;
    said cassette mechanism and said cassette thus interfacing when connected so that said occluder shaft of the irrigation solenoid passes through the irrigation opening of the cassette to occlude said irrigation manifold against said leading edge surface of said irrigation boss, thereby to control flow of irrigation fluid through said irrigation manifold; and so that the roller assembly of said aspiration pump occupies said aspiration pump opening of said cassette and occludes said aspiration manifold against said aspiration boss, thereby to control the aspiration of fluid through said aspiration manifold; said VCS fitting connecting with said VCS opening in a sealing manner.

2. A cassette for surgical irrigation and aspiration for use in cooperation with an apparatus which includes an irrigation control means for controlling a flow of irrigation fluid to an operative site, aspiration control means for controlling flow of aspirating fluid from an operative site, and vacuum control means for controlling the aspiration of such fluid from the operative site, comprising:
    a housing having an edge defining an irrigation opening, an aspiration pump opening, and a vacuum control system (VCS) opening, said housing containing at least a portion of an irrigation manifold and an aspiration manifold which are structurally adapted and arranged within the housing so that, when the cassette is inserted into a predetermined cassette opening in said apparatus, said irrigation control means controls the flow of irrigation fluid through said irrigation manifold; said aspiration control means controls the flow of aspiration fluid through said aspiration manifold; and said vacuum control means controls the vacuum applied to said aspiration manifold, and
    wherein said housing includes an aspiration boss located in register with said aspiration pump opening, wherein a portion of said aspiration manifold is located intermediate said aspiration boss and said aspiration opening so that a pumping portion of an aspiration pump of said aspiration control means can effect pumping of aspirated fluid through said aspiration manifold.

3. The cassettes as set forth in claim 2, wherein said cassette includes an irrigation boss defining a control surface located in register with said irrigation opening so that, upon insertion of said cassette into said predetermined cassette opening, said irrigation control means controls the flow of irrigation fluid in said irrigation manifold by coacting with said irrigation boss.

4. The cassette as set forth in claim 3, wherein a portion of said irrigation manifold is located intermediate said control surface of said irrigation boss and said irrigation opening so that an occluding member of said irrigation control means can mate therewith to occlude flow of fluid through said irrigation manifold.

5. The cassette as set forth in claim 2, further including means for securing a drainage bag on the trailing edge of said cassette, said securing means including a plurality of drainage bag bosses and a drainage bag holddown for securing said drainage bag with said cassette.

6. The cassette as set forth in claim 2, wherein said aspiration manifold includes a VCS connector connected to said VCS opening on the leading edge of said cassette.

7. The cassette as set forth in any one of claims 2-6, further in combination with a cassette mechanism mounted on said apparatus for receiving said cassette therein, said cassette mechanism comprising a cassette latch member and means secured to said cassette latch member for mounting an irrigation solenoid, an aspiration pump and roller assembly, and a VCS fitting thereon in such a manner that irrigation, aspiration and vacuum fluidic connections are made upon insertion of said cassette into said cassette mechanism.

8. The combination as set forth in claim 7, wherein said aspiration and roller assembly is mounted to said mounting means by way of a bearing mounting plate defining a slot and including a beveled arm.

9. The combination as set forth in claim 8, further including a cassette latch bracket for latching an opening in the housing of said cassette.

10. The combination as set forth in claim 9, further including means for releasing said latch.

11. The combination as set forth in claim 9, further including a cassette latching mechanism comprising a release arm, linkage, and a plurality of latch arms, the trailing edges of which are beveled, and structurally arranged so that insertion of said cassette into said cassette mechanism causes movement of the trailing edges of said latch arms downward and beneath the cassette.

12. In combination, a cassette for surgical irrigation and aspiration for use in cooperation with an apparatus which includes an irrigation control means for controlling a flow of irrigation fluid to an operative site, aspiration control means for controlling flow of aspirating fluid from an operative site, and vacuum control means for controlling the aspiration of such fluid from the operative site, comprising:
    a housing having an edge defining an irrigation opening, an aspiration pump opening, and a vacuum control system (VCS) opening, said housing containing at least a portion of an irrigation manifold and an aspiration manifold which are structurally adapted and arranged within the housing so that, when the cassette is inserted into a predetermined cassette opening in said apparatus, said irrigation control means controls the flow of irrigation fluid through said irrigation manifold; said aspiration control means controls the flow of aspiration fluid through said aspiration manifold; and said vacuum control means controls the vacuum applied to said aspiration manifold;

said cassette being in combination with a cassette mechanism mounted on said apparatus for receiving said cassette therein, said cassette mechanism comprising a cassette latch member and a solenoid/pump mounting means secured to said cassette latch member for mounting an irrigation solenoid, an aspiration pump and roller assembly, and a VCS fitting thereon in such a manner that irrigation, aspiration and vacuum fluidic connections are made upon insertion of said cassette into said cassette mechanism.

13. The cassette as set forth in claim 12, wherein said cassette includes an irrigation boss defining a control surface located in register with said irrigation opening so that, upon insertion of said cassette into said predetermined cassette opening, said irrigation control means controls the flow of irrigation fluid in said irrigation manifold by coacting with said irrigation boss.

14. The cassette as set forth in claim 13, wherein a portion of said irrigation manifold is located intermediate said control surface of said irrigation boss and said irrigation opening so that an occluding member of said irrigation control means can mate therewith to occlude flow of fluid through said irrigation manifold.

15. The cassette as set forth in claim 12, further including means for securing a drainage bag on the trailing edge of said cassette, said securing means including a plurality of drainage bag bosses and a drainage bag holddown for securing said drainage bag with said cassette.

16. The cassette as set forth in claim 12, wherein said aspiration manifold includes a VCS connector connected to said VCS opening on the leading edge of said cassette.

* * * * *